US007083653B2

(12) United States Patent
Jennings

(10) Patent No.: US 7,083,653 B2
(45) Date of Patent: Aug. 1, 2006

(54) IMPLANTABLE HUMAN KIDNEY REPLACEMENT UNIT

(76) Inventor: Charles Edward Jennings, 1330 Heathwick La., Houston, TX (US) 77043

( * ) Notice: Subject to any disclaimer, the term of this patent is extended or adjusted under 35 U.S.C. 154(b) by 119 days.

(21) Appl. No.: 10/916,586

(22) Filed: Aug. 12, 2004

(65) Prior Publication Data

US 2006/0036332 A1 Feb. 16, 2006

(51) Int. Cl.
*A61F 2/04* (2006.01)
(52) U.S. Cl. .................................................. 623/23.65
(58) Field of Classification Search ............. 623/23.65, 623/23.66, 23.64
See application file for complete search history.

(56) References Cited

U.S. PATENT DOCUMENTS

| | | | | |
|---|---|---|---|---|
| 4,183,811 A * | 1/1980 | Walch et al. ................ 210/646 |
| 4,222,869 A * | 9/1980 | Kato .......................... 210/646 |
| 4,354,933 A * | 10/1982 | Lester ..................... 210/257.2 |
| 4,634,447 A * | 1/1987 | Isono et al. ............... 623/23.65 |
| 4,648,865 A * | 3/1987 | Aigner ...................... 604/6.09 |
| 4,769,037 A * | 9/1988 | Midcalf .................... 623/23.65 |
| 5,092,886 A * | 3/1992 | Dobos-Hardy ........... 623/23.65 |
| 5,284,470 A * | 2/1994 | Beltz ......................... 604/4.01 |
| 5,397,354 A * | 3/1995 | Wilk et al. ..................... 604/28 |
| 5,549,674 A * | 8/1996 | Humes et al. ........... 623/23.65 |
| 5,813,410 A * | 9/1998 | Levin .......................... 128/897 |
| 5,944,684 A * | 8/1999 | Roberts et al. ............ 604/5.04 |
| 5,980,480 A * | 11/1999 | Rubenstein et al. ........... 604/9 |
| 6,168,578 B1 * | 1/2001 | Diamond ..................... 604/29 |
| 6,234,991 B1 * | 5/2001 | Gorsuch ...................... 604/29 |
| 6,613,095 B1 * | 9/2003 | Levin ...................... 623/23.65 |
| 6,623,441 B1 * | 9/2003 | Kihara et al. .............. 604/4.01 |
| 6,960,179 B1 * | 11/2005 | Gura .......................... 604/6.09 |
| 2005/0273031 A1* | 12/2005 | Ueno et al. ................ 604/6.08 |

* cited by examiner

*Primary Examiner*—Alvin J. Stewart

(57) ABSTRACT

An implantable human kidney replacement unit. Fully functional self contained, providing patients with end stage renal disease the freedom of traveling and moving about normally. Replacing donor kidneys. Implanted in the flank with at least one inlet and outlet tube each, sutured to the iliac artery and vain, at least one urine tube to the ureter. The housing constructed of anti-coagulant bacteriostatic materials has a plurality of reverse-osmosis process chambers with semipemeable membranes through the unit, followed by osmosis-diffusion chambers and membranes. Blood from the artery enters the first of the chambers. Small molecules such as water, magnesium, sodium, potassium, calcium, urea etc. are extracted from the blood according to their weight in atomic mass units as blood wipes past the self-cleaning membrane cartridges in the chambers. Molecules are further separated and urea sent to the bladder with excess water and electrolytes. The remainder is channeled to at least one diffusion chamber and reabsorbed into the blood. The same process is repeated in the other chambers where selected larger molecules such as creatinine and phosphorus are excreted, and some diffused back into the blood.

18 Claims, 3 Drawing Sheets

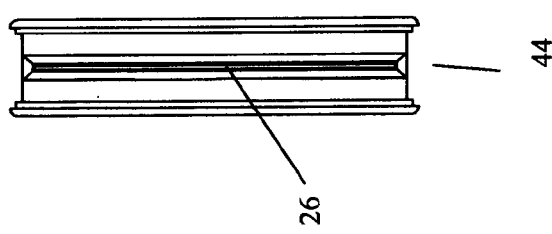
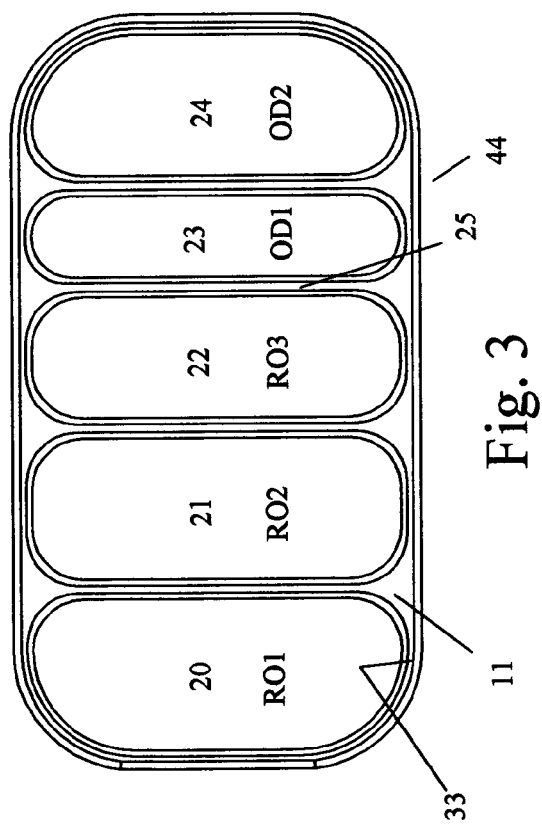
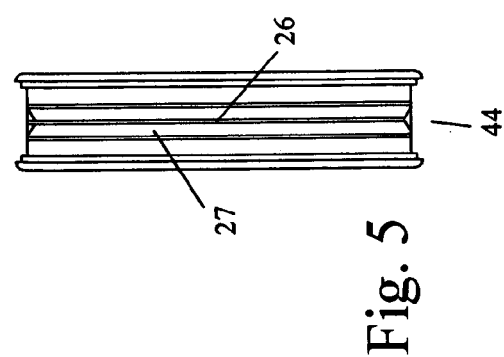
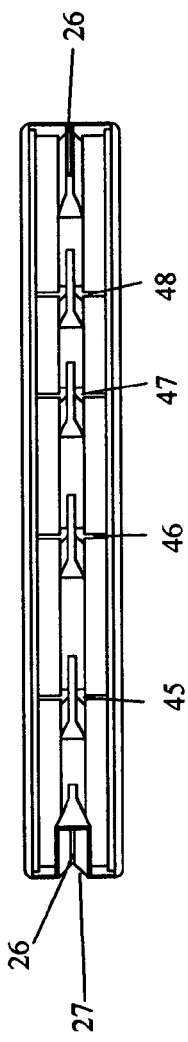

IMPLANTABLE HUMAN KIDNEY REPLACEMENT UNIT

This patent application is based upon U.S. provisional patent application Ser. No. 60/493,926, filed Aug. 11, 2003, titled Implantable Human Kidney Replacement Unit.

BACKGROUND OF THE INVENTION

1. Field of the Invention

This invention relates in general to an implantable artificial kidney, more particularly a miniature life-sustaining blood purifying hemocatharsais unit, maintaining acceptable homeostasis when implanted in patients with chronic end stage renal disease, sutured to a major artery, vein and ureter, functions with no extra-corporeal connections nor interactions. Obtainable without a living or cadaver donor, eliminating the required 0 to 6 antigen matching and the immunosuppressive, anti-rejection medication required for the lifespan of all donated human kidneys.

2. Background of the Invention

The Human Urinary System is made up of the kidneys, the bladder, two ureters, and a single urethra. The kidneys are a pair of organs resembling large kidney beans. In the average adult, measuring around 4" to 5" long and 2" to 3" wide, and situated against the rear wall of the abdomen, in the middle of the back, located on either side of the spine, beneath the liver on the right, and the spleen on the left.

Healthy kidneys in the average adult process about 125 ml/min or 180 liters of blood each day to filter out about 2 liters of waste product and extra water in the urine. The kidneys remove excess minerals and wastes and regulate the composition of the blood by keeping the concentrations of such inorganic ions as sodium, phosphorus, and chloride in the blood plasma at a nearly constant level. Potassium is controlled by the kidneys, for proper functioning of the nerves and muscles, particularly those of the heart.

Blood urea nitrogen (BUN), a waste product produced in the liver as the end product of protein metabolism, is removed from the blood by the kidneys in the Bowman's capsule, along with Creatinine a Waste Product of creatinine phosphate, an energy storing molecule, produced largely from muscle breakdown. High values, especially with high BUN levels indicate problems with the kidneys. When the kidneys are functioning properly and the concentration of an ion in the blood exceeds its kidney threshold value, the excess in the filtrate is not reabsorbed but is released in the urine thus maintaining near constant levels, the same is so with excess protein. This is done by the mechanisms of reverse osmosis, osmosis and ion exchange filtration.

Most kidney diseases attack the nephrons, causing them to loose their filtering capacity. The two most common causes of kidney disease are diabetes and high blood pressure. Diabetes keeps the body from using glucose as it should. If glucose stays in the blood instead of breaking down, it can act like poison and damage the nephrons. High blood pressure can damage the small blood vessels in the nephrons. The damaged vessels cannot filter poisons from the blood as they should. If the problems worsen and renal function drops below 10 to 15 percent, that person has end stage renal disease. When a persons kidneys fail, harmful wastes build up in their body, their blood pressure elevates and the body retains fluid.

That person will soon die unless their life is temporarily prolonged by either a kidney transplant or dialysis. If the patient chooses a kidney transplant their immune system attacks the foreign kidney, requiring that the patient take immunosuppressants the rest of their life. If the patient chooses dialysis their electrolytes, especially phosphorus will become unmanageable; this plays a big role in the cardiovascular mortality rate being 20 to 40 times higher for adults on dialysis than for the general population.

Dialysis machines are the most widely used temporary lifesaving invention for patients with end-stage renal disease. Hemodialysis machines are described as large stationary hydro-mechanical devices. In order to make them functional they require many accessories such as an arterial line, blood pump, heparin infusion pump, dialyzer filter, venous line, monitors to measure blood flow and pressure, air/foam detectors, motors, regulators and piping to carry 500 to 800 mL/min of dialysis solution with water and measured amounts of calcium, magnesium, sodium, potassium and other minerals, from large mixing-holding vats to the patients dialyzer, and from there to the drain. With hemodialysis the patient must be dialyzed three times a week; each treatment lasting from three to four hours. Although the dialyzers are removing poisons, there are side effects caused primarily by the dialyzers themselves.

The dialyzer filters are made of cellulose acetate, polysulfone or similar materials and sterilized with a solution of ethylene oxide, bleach or formaldehyde, none of which is suitably biocompatible. Dialyzer filters have just one membrane pore size with a cut-off point just larger than creatinine at 113.12 atomic mass units (AMU). Removed with the creatinine is urea at 60.06 AMU, water and essential electrolytes such as sodium, potassium, calcium and magnesium are removed by the dialyzer but not replaced during dialysis.

Phosphorus molecules at 123.92 AMU, are not removed by dialysis and large amounts are deadly to the patient. Neither failed kidneys nor dialysis can remove phosphorus, requiring that large doses of calcium based phosphate binders be taken, leading to coronary calcification and eventual death for many dialysis patients. Other problems with dialysis is that the tubing blood pump crushes many of the patient's blood cells, inducing clotting, the machine is also known for overheating the patients blood.

3. Brief Summery of the Invention

This invention relates in general to a fully functional human kidney replacement unit, made of anticoagulant materials. Comparable in size to actual human kidneys. This device will provide patients who have end stage renal failure with an alternative to donor kidneys (graft), without having to combat rejection by taking immunosuppressive agents, often accompanied by side effects and infection. This kidney replacement unit whether worn outside the body extracorporeal, or implanted in the body by surgery, will provide patients with essential kidney functions, similar to those of real kidneys.

Unlike large cumbersome dialysis machines requiring long arterial lines, blood pumps and heparin infusion pumps, a dialyzer cartridge, venous line, blood flow monitors, pressure and air/foam detectors, and to further worsen the situation, the patient is troubled with hypertension, hypotension, headaches, nausea, blood loss, blood overheating, Blood imbalance, shortness of breath, respiratory arrest, itching, hives, edema, elevated pulse rates and arrhythmia, and unlike this invention with multiple membranes, dialysis machines have only one membrane pore size which is In the range of 117 AMU, sized to remove createnine at 113 AMU. Unfortunately at the demise of the patient, these large pores remove the smaller essential electrolytes and minerals such as sodium, potassium, bicarbonate, calcium and magnesium. Dialysis also removes vitamin B12, folic acid and pyrodoxin, essential in maintaining good health.

In the preferred embodiment, the implantable human kidney replacement unit, referred to hereafter in this disclosure as "the unit" though compact and smaller than human kidneys, contains a plurality of independent self cleaning membranes fixed in cartridges designed to sort and reject or re-inject certain molecules as regulated by the patients needs. Selecting molecules by their weight in atomic mass units, waste products such as creatinine and urea, are removed while homeostasis in the blood is maintained by keeping the volume of water in the body constant. This invention regulates the concentration of electrolytes in the blood, such as the positive sodium, calcium, potassium and magnesium cations, and the negative chloride, bicarbonate, phosphorus and sulfate anions.

When the concentration of an ion in the blood exceeds the threshold value, the excess in the filtrate is not reabsorbed but is released in the urine, thus maintaining near constant levels in the blood. The unit housing is constructed of smooth crack and leak resistant blood compatible materials. Preferably polyvinyl-chloride (PVC) co-polymer, having anti-coagulant and bacteriostatic properties. All the interior blood passages are without sharp corners and edges that would cause turbulence and damage the blood cells, thus inducing clotting.

The units case contains all the porting and slots for blood and filtrate pressure regulation and distribution to and from a plurality of individual membrane filters made of inert anti-coagulant materials, preferably platinum, affixed one on each side of individual frames, forming membrane cartridges. There is at least one cartridge sealed to each side of each glomerular chamber, referred to mostly hereafter in this disclosure as "chambers". There is an overflow port and a pressure relief valve in the upper end of each cartridge. To maintain positive pressure, slightly less than arterial pressure in the chambers.

Blood leaving the first chamber is cleaner than when it entered. Pressure rises in the cartridge cavity between the two membranes because the larger molecules that penetrated the first membrane are too large to pass through the outer membrane, the pressure relief valve opens and urine spills over into the waste port down through the chamber dividers, next to but not intersecting the vertical slit. The vertical narrow slit in the divider between chambers reverse osmosis chamber (RO) three and osmosis-diffusion (OD) chamber four is not as wide as those in the first three RO chamber dividers.

This is to reduce the pressure in the OD chambers, while raising the pressure in the filtrate-collection annular space; therefore, the process occurring now in OD chambers four and five is osmosis and diffusion, where molecules are being selectively reabsorbed into the blood as needed.

The process taking place in chambers four (OD-4) and five (OD-5) Is "dynamic diffusion" which occurs when some of the water and substances such as sodium and calcium flow from a region where they are highly concentrated to a region of lesser concentrated until a state of equilibrium is reached. Diffusion occurs when a system is not at equilibrium, as is the blood substances in chambers four and five and the filtrate substance from the RO chambers, separated by semi-permeable membranes in cartridges four and five. Osmosis is the diffusion of liquid molecules across a semi-permeable membrane. All molecules not diffused and reabsorbed in chambers four and five will be forced out the valves in the top of the membrane cartridges and drain down through the vertical cavity, to the waste chamber and then to the ureter and bladder.

Ficks first law of diffusion states that a substance diffuses in the direction that eliminates its concentration gradient at a rate proportional to the magnitude of its gradient. It is the square of the distance that has an influence on the formula and it is proportional to the available area. The IAK membranes have short distances and large areas to speed the diffusion process.

BRIEF DESCRIPTION OF THE DRAWINGS

So that the manner in which the features, advantages and objects of the invention, as well as others which will become apparent, are attained and can be understood in more detail, a more particular description of the invention briefly summarized above may be had by reference to the embodiment therefore which is illustrated in the appended drawings, which drawings form a part of this specification. It is to be noted, however, that the drawings illustrate only a preferred embodiment of this invention and is therefore not to be considered limiting of its scope as the invention may admit to other equally effective embodiments.

FIG. 3 is the main housing frame show from side A. The large through-holes are the independent glomerular process chambers (minus the membrane cartridges) of varying sizes. Each glomerular chamber is partitioned by thin dividers. A narrow slit extends through all the dividers for blood communication in the inlet, between the chambers, and out the discharge end. Around the circumference of each chamber, on both sides, are ledges where the membrane cartridges will seal.

FIG. 4 is the main housing viewed from the bottom, without both the cover and the urine discharge tube.

FIG. 5 is the main housing from the blood inlet end, without the inlet tube and distribution cover, exposing the extended narrow blood distribution slit into the $1^{st}$ chamber.

FIG. 6 is main housing from the blood exit end without the urine discharge tube and collection cover, showing the extended narrow blood outlet collection slit.

The upstream side (left side) is beveled all around to funnel blood to the slot. The first three glomular process chambers from left to right are reverse osmosis (RO) chambers and are labeled RO1, RO2 and RO3, also shown numerically as 20,21 and 23. The other two chamber to the right are osmosis diffusion chambers and are labeled OD1 and OD2, shown numerically as 23 and 24. There are five membrane cartridges in the assembly, six reverse osmosis cartridges, three on side A labeled RO1-A, RO2-A, and RO3-A, and three on side B, labeled RO1-B, RO2-B and RO3-B. Four osmosis-diffusion cartridges. Two on side A labeled OD1-A and OD2-A, and on side B they are OD1-B and OD2-B Looking down at the main housing is vertical cavities running through the chamber dividers. This is where waste, excess water or other chemicals are allowed to drain down to a waste chamber beneath the glomular chambers on the bottom of the main housing. On both sides, (A) and (B) of the glomular chambers in the main housing are recesses with the same geometry as the chambers but slightly larger in height and width, forming an all around ledge. These ledges are where the membrane cartridges will be housed and sealed. Further out near the outer edge on both side (A) and (B) is one large recess extending the full width and height of the main housing, except for a thin lip all around the parameter. This is where the main covers nest and seal.

DETAILED DESCRIPTION OF THE PREFERRED EMBODIMENT

Figure 2:
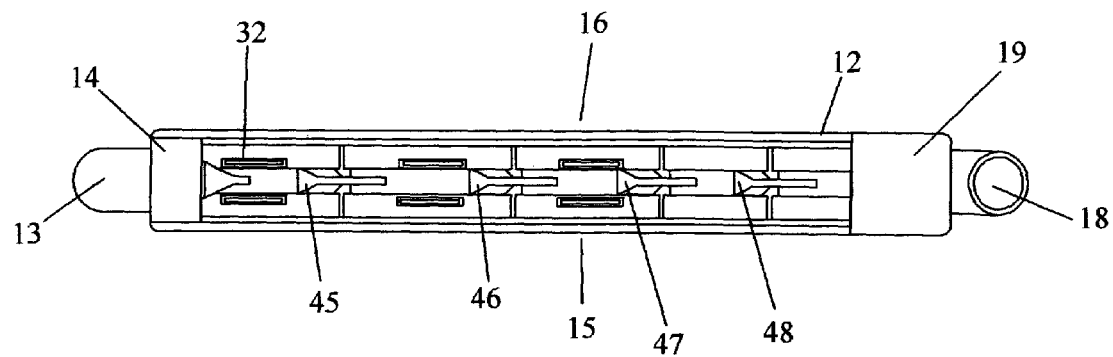
FIG. 2 is a top view of the unit's housing assembly. Shown through the top cover is the rectangular pressure valves from the membrane cartridges Shown also is the waste discharge ports extending vertically from the top of the housing, through the glomerular chamber dividers (not shown) to the urine collection area at the bottom of the housing assembly.
Figure 1:
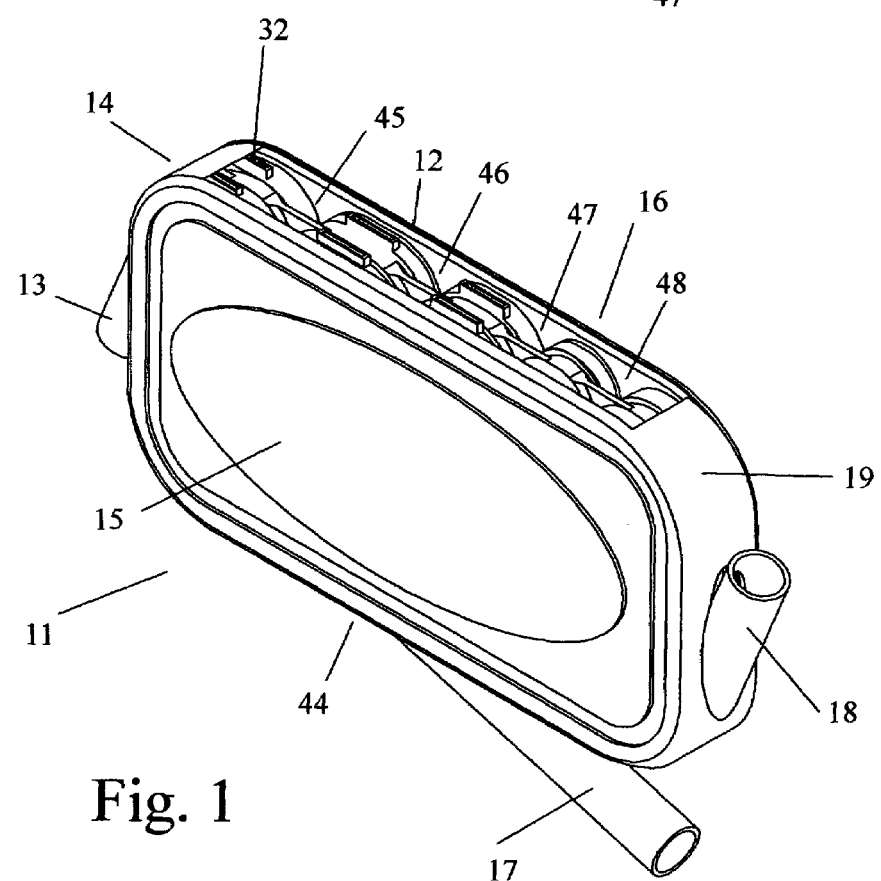
FIG. 1 is the assembly of the implantable human kidney replacement unit constructed in accordance with the embodiment of the invention, shown from side A, on the left is the inlet tube for directing toxic blood from the patients iliac or other major artery. Shown on the right of the assembly is the outlet tube for directing clean conditioned blood from the unit, into the patients iliac or other major vain. The urine discharge tube is shown on the bottom right. It is for directing waste products such as creatinine, urea and excess water in the filtrate to the ureter. Side B not shown, is a mirror image of side A.

Referring now to the drawings, wherein the preferred embodiment of this invention, the implantable human kidney replacement unit, to be referred to in this disclosure as 'the Unit", is depicted in the perspective view of FIG. 1 as item 11, made in accordance with the specifications outlined herein. Item 12 are the main support frame wherein all the other components are sealingly connected. Beginning to the left of FIG. 1 the blood inlet tube 13 from the ileac (or other) major artery terminates into and becomes integral to the blood inlet distribution cover 14, in turn sealed to frame 12.

Also Sealed to side A and side B of frame 12 is filtrate cover plates 15 and 16, for retaining and channeling filtrate from the blood plasma. On the blood outlet end of unit 11 is tube 18, formed integral with blood collection cover 19, sealed to frame 12, from there, tube 18 is sutured to the patients iliac or other major vain. Item 44 are the waste chamber cover formed integral with urine discharge tube 17. Tube 17 is sutured to the patient's ureter. Top cover 29 (not shown) is removed, exposing waste drain ports 45, 46, 47, and 48 extending through the chamber dividers 25 of frame 12 in FIG. 3, and intersecting waste chamber 44. Item 32 is the pressure regulated waste discharge ports extending through frame 12.

Figure 7:
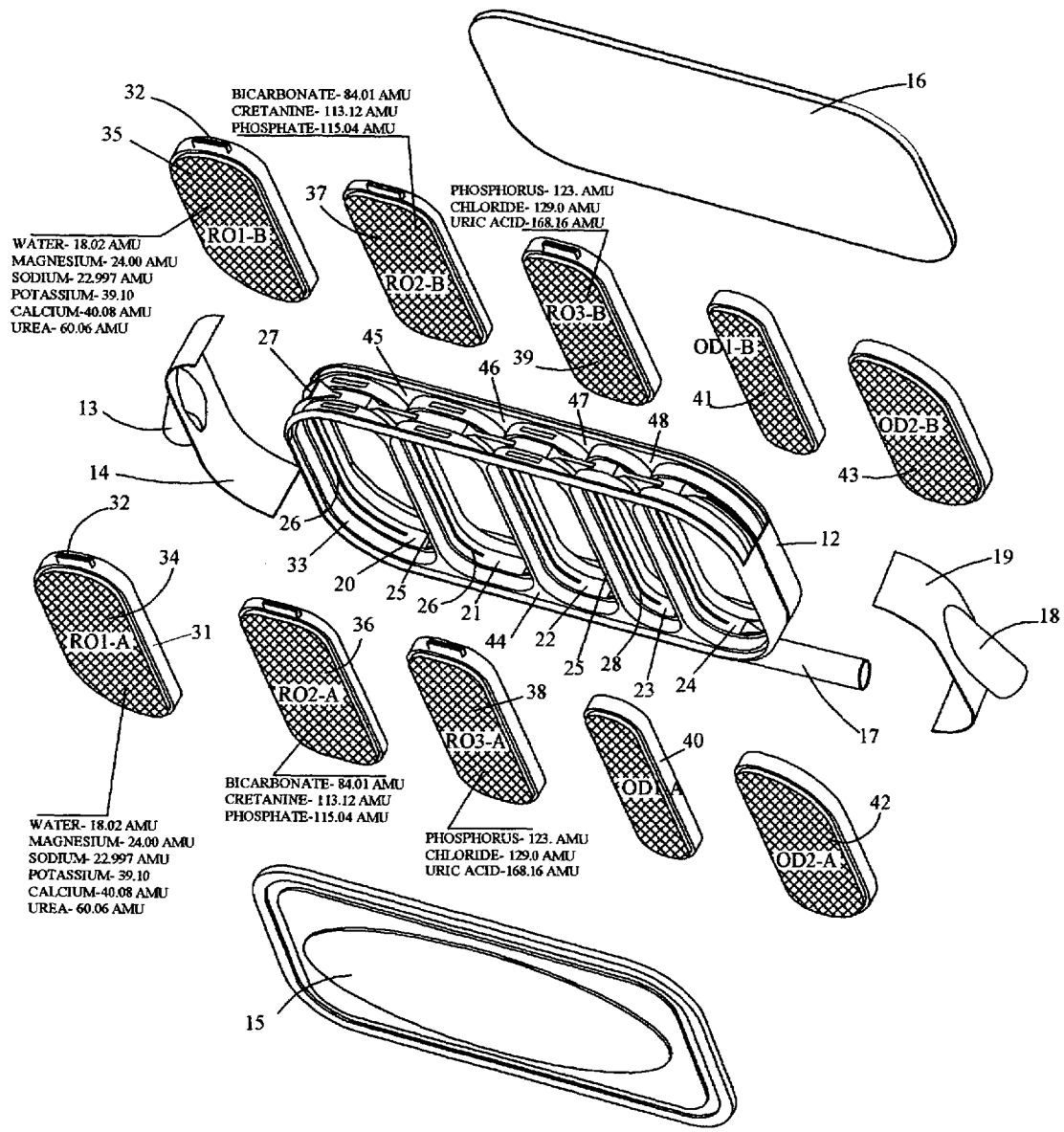
FIG. 7 is an exploded view of the main housing assembly, showing the double membrane cartridges, the end caps with the blood inlet and outlet tubes, the front and rear cover seal plates A and B and the urine outlet tube on the bottom right hand side. Listed on the drawing is the major substances and the molecule sizes in AMU units, that will be processed in the membrane cartridges. Shown again in this view, running horizontally through the vertical chamber dividers is the narrow slit, extending the full height of each chamber. All the edges of the slit are chamfered or rounded to eliminate sharp corners that could damage the blood, or cause turbulence.

Assembly frame 12 is shown in FIGS. 3 and 4 stripped of all covers and components exposing process chamber openings 20, 21, 22, 23 and 24. Each chamber opening is separated by a divider 25, providing also a means for housing vertical cavities 45, 46, 47, and 48 which extend from the top of the unit, beneath cover 29, to waste collection area 44 at the bottom of unit 11. Integral to frame 12 are two profile ledges 33 (one on each side), provided in each chamber opening, where membrane cartridges as shown in FIG. 7 as RO1-A etc. are inserted and sealed. In 12, intersecting and extending the full height of chamber dividers 25 are blood pressure and flow regulating slits 26, each slit having channeling bevel 27 on the blood inlet side.

Frame 12 of assembly 11 viewed from the bottom in FIG. 4 shows the blood inlet distribution and pressure-regulating slit 26 on the left, with funneling bevel 27, better distinguished in FIG. 5. FIG. 6 is viewed from the blood outlet side of frame 12 without the blood outlet tube 18 and collection cover 19 as shown FIG. 1. In order to clarify the sequence of events occurring in the blood purifying an processing occurring in this unit, the membrane chamber and cartridge assemblies are identified as RO for reverse osmosis and OD for osmosis-diffusion followed by a number to identify the sequence in which it follows and, an A or B to identify the side it is on.

Example, on the A side of chamber 20 is cartridge 34, labeled RO1-A and on the B side is cartridge 35 labeled set RO1-B. The number 1is because it is first in the reverse osmosis sequence. The pore sizes in the two membranes in the RO cartridges are different. The inside membranes have a larger molecule cut-off size than the outside membranes. This will cause molecules that passed through the inside membrane, into cavity 31 between the inner and outer membrane, too large to pass through the outside membranes, exhaust out the top of cavity 31 through overflow relief valve 32 when the pressure rises enough to open the valve. This is how the waste products are moved into the waste drain ports.

Referring now to FIG. 7. After the unit 11 is successfully surgically implanted in the patient, blood from the patient's iliac artery flowing at normal pressure enters chamber 20 of assembly 11 through inlet tube 13 and distribution cover 14, past channel bevels 27 through the first narrow vertical slit 26. This full height distribution of slot 26 causes blood to flow fully and evenly across the whole face of the inner membranes of sets RO1-A and B, of cartridges 35 and 35 in chambers 20 and 21, creating a wiping action, breaking loose larger molecules in the blood that tend to block the membrane pores.

Slits 26 in the chamber dividers are also sized to regulate the blood flow at the inlet and outlet of each chamber and maintain positive pressure in the chambers between the RO cartridge membranes, forcing selected molecules from the blood plasma. The last RO chamber in the series communicates with the first osmosis diffusion (OD) chamber through a slit sized to balance the pressure in the OD chambers with the plasma filtrate outside the chamber cartridges semipermeable membranes, setting up the diffusion process for re-absorption of water and selected substances into the blood.

As blood flows smoothly into the narrow center chamber 20, of housing 12, between cartridges 34 and 35 (membrane set RO1-A and B) normal blood pressure forces some of the molecules in the plasma smaller than 65 AMU, through the pores of the inner cartridge membranes, into center cavity 31 of the cartridges, this includes water at 18.02, AMU magnesium at 24 AMU, sodium 22.9 AMU, potassium 39.10 AMU, calcium 40.08 AMU, and the poison urea 60.06 AMU. The pores in the outer cartridge membranes are smaller than 50 AMU, allowing all the molecules that entered the center cavity 31 of cartridges 34 and 35 through the inside membrane (1$^{st}$ in the pair), but Urea at 60.06 AMU, to pass through the pores in the outer membrane into the filtrate collecting area beneath filtrate cover plates 15 and 16 to be reabsorbed in areas OD-4 and OD-5 as needed.

When center cavity 31 (space between the membrane pairs) of cartridges 34 and 35 are dense with urea at 60.06 AMU, molecules temporarily blocking the pores in the outer membranes cause the pressure in center cavity 31 to rise enough to open the upper pressure valve 32 and allow Urea to spill over into waste port 45 running down through chamber divider 25, next to but not intersecting slit 26. Somewhat cleaner blood flows from chamber 20, into the second chamber, 21 through the second narrow vertical slit 26, penetrating divider 25.

The pores in the inner membranes in set RO2-A and B of cartridges 36 and 37 are sized to allow bicarbonate at 84.01 AMU, creatinine at 113.12 AMU and phosphate at 115.04 AMU, into the center cavity 31. These, along with some of the smaller molecules like water 18.02, magnesium 24.00, sodium 22.997, calcium 40.08, potassium 39.10 and traces of urea, also penetrate the inner membranes, moving into center cavity 31 of both RO2 cartridges. The cut off size for molecules allowed to pass through outer membrane RO2 is anything above 85.00 AMU. This will not allow passage of waste products like createnine at 113.12 AMU and phosphate at 115.00 AMU.

The outer membranes of sets RO2 A and B of cartridges 36 and 37 are sized to pass bicarbonate at 84.01AMU and smaller, but not phosphate at 115.04 AMU and creatinine at 113.12. When the concentration in the center cavity 31 causes the pressure to increase enough to open the relief valve 32, phosphate and creatinine will spill out the top, into drain port 46, then down to the urine collection area 44. Excreting much of the phosphate here is good, since most foods contain large quantities, and with this invention, kidney replacement unit, the patient will not be required to take calcium phosphate binders.

Blood leaves glomerular chamber 21 and enters chamber 22 through the third narrow vertical slit 26, penetrating the divider between the RO2 to RO3 cartridge membrane sets. glucose at 180.16 AMU will not be removed from the blood here because most of it is required in the bloodstream anyway and would have to be reabsorbed in chamber 24, OD5 later. The pores in the inner membranes of cartridges RO3 are sized to pass phosphorus at 123.92 AMU, chloride at 129 AMU and uric acid at 168.16 AMU, into the cartridge's center cavities 31.

The number of molecules passing through the membranes is proportional to the concentration in the blood. The more molecules there are, the more are removed. When the concentration in the blood is low, very little phosphorus, chloride and uric acid will be removed, They will only be removed when the concentrations are too high. Therefore the pores in the outer membranes of sets RO3 A and B are sized to block molecules larger than 100 AMU, allowing water 18.02, bicarbonate 84.01, and other electrolytes to pass through as filtrate to be selectively reabsorbed into the blood in the osmosis-diffusion cartridges sets OD4 and OD5 later.

As the density rises in the center cavity of cartridges RO3-A and B, the upper pressure relief valve 32 opens, allowing excess phosphorus, chloride and uric acid to spills out the top, into drain port 47 leading to the urine collection area 44. At this time the reverse osmosis chambers are filled, pressurized and expelling selected molecules from the blood, which are stored outside the cartridges behind filtrate cover plates 15 and 16 in the pressurized annular space.

The vertical narrow slit 26 in the divider between reverse osmosis chamber RO3 and osmosis chamber OD4 is approximately 0.002 wide instead of the approximate 0.005 wide in the first three dividers. This is to reduce the pressure in chamber 23, which is the location of cartridges 40 and 41 and membrane sets OD4 A and B. Referring again to FIG. 7. All the filtrate from the RO cartridge membrane sets, including water 18.02, magnesium 24.00, sodium 22.997, potassium 39.10, calcium 60.06, bicarbonate 84.01 has collected on the outside of membrane cartridge sets OD1 and OD2-A and B, in the pressurized filtrate-collection space beneath cover plates 15 and 16.

The filtering process in chambers OD4 and 5 is osmosis and diffusion, where molecules are selectively absorbed into the blood instead of being forced from the blood as in the reverse osmosis chambers. The pore sizes in membranes OD1 A and B are sized to absorb molecules up to 45 AMU, and up to 100 AMU in OD2 A and B. All substances not absorbed there will spill over the top and drain down port 48 and be excreted in the urine. With the substances re-entering the blood in chamber 23 through the OD1 membranes, pressure rises there, so slit 26 is now wider through divider 25 located between chambers 23 and 24.

Molecules of substances too large to be absorbed through membranes OD1 but small enough to diffuse through OD2 will be reabsorbed in chamber 24, where the blood pressure is back to normal as the clean reprocessed blood is discharged through tube 18, sutured to the iliac or other major vain. The science taking place in chambers OD4 and OD5 Is dynamic diffusion which occurs when some of the water, and substances such as sodium, and calcium flow from the region where they are highly concentrated to a the region where they are less concentrated, until a state of equilibrium is reached. Diffusion occurs when a system is not at equilibrium, as is the case in process chambers OD4 and OD5 , enhanced by the pressure balancing effect of the flow control and distribution slits 26 and the pressure relief valve 32, adjusting the blood pressure inside glomerular chambers 23 and 24 so as to be slightly negative as compared to the filtrate pressure exhausting at RO 1, 2 and 3 now outside the semi permeable membranes cartridges OD4 and 5 beneath, cover plates 15 and 16.

FICK's First Law of Diffusion states that a substance diffuses in the direction that eliminates its concentration gradient at a rate proportional to the magnitude of its gradient. It is the square of the distance that has an influence on the formula and it is proportional to the available area. The unit's membranes have short distances and large areas to speed the diffusion process. While the invention has been shown in only some of its forms, it should be apparent to those skilled in the art that it is not so limited, but is susceptible to various changes without departing from the scope of the invention. For example the same invention could have the membranes configured in any number of shapes and sizes.

What is claimed is:

1. an implantable human kidney replacement unit comprising in combination:

an outer housing;

a support frame mounted inside the housing;

a blood inlet port in said housing, located at one end of the housing;

a blood discharge port in said housing, spaced apart from the blood inlet port;

a urine waste discharge port in said housing, located at a generally lower end of the housing;

at least one arterial inlet tube for joining to a patient's iliac or other major artery on one end and sealingly connecting to the blood inlet port;

at least one venous discharge tube connected to the blood discharge port at one end for joining to the patient's iliac or other major vein on opposite end;

at least one urine discharge tube connected to the urine waste discharge port on one end for joining to the patient's ureter at opposite end of said urine discharge tube;

a plurality of reverse osmosis filtration membranes located in the housing and support frame; and a plurality of osmosis-diffusion membranes located in the housing and support frame.

2. An implantable human kidney replacement unit comprising in combination:

an outer housing;

a support frame mounted inside the housing;

a blood inlet port in said housing, located at one end of the housing;

a blood discharge port in said housing, spaced apart from the blood inlet port;

a urine waste discharge port in said housing, located at a generally lower end of the housing;

at least one arterial inlet tube for joining to a patient's iliac or other major artery on one end and sealingly connecting to the blood inlet port;

at least one venous discharge tube connected to the blood discharge port at one end for joining to the patient's iliac or other major vein on opposite end;

at least one urine discharge tube connected to the urine waste discharge port on one end for joining to the patient's ureter at opposite end of said urine discharge tube;

a manifold formed integral with said support frame, said manifold having a plurality of socket chambers aligned side by side, separated by dividers, having slits penetrating the divider through full height of said divider, located halfway through said socket chamber, providing a means for arterial blood to enter and exit said chambers.

3. The invention according to claim 2 further comprising said manifold arranged with a plurality of membrane cartridges to perform reverse osmosis and diffusion with arterial blood, and with said membrane cartridges to separate the molecules to be excreted as waste and some reabsorbed into the blood.

4. The invention according to claim 3 where said slit controls flow and pressure and comprises a means to regulate the arterial blood pattern through said chambers, between pairs of membranes cartridges.

5. The invention according to claim 4 in which a membrane cartridge divider frame assembly comprises sides and ends to form a cavity between said membranes.

6. The invention according to claim 5 in which said membrane cartridge divider frame, comprises at least one exit port having at least one pressure relief valve fixed to open and exhaust from inside said cavity at a predetermined pressure, the cartridges having membranes on opposite sides of divider frame from each other with different AMU values.

7. The invention according to claim 6 comprising cover means to seal in a plasma filtrate outside the reverse osmosis membranes and spill over from membrane cartridge a wastestream, allowing filtrate to be either channeled to be reabsorbed into the bloodstream through the osmosis diffusion membranes, or be excreted in the urine.

8. The invention according to claim 2 wherein said slit further comprises a flow control regulator to regulate blood pressure in the chambers relative to plasma filtrate pressure outside the cartridge membranes in said chambers.

9. The invention according to claim 2 wherein said slit is beveled to direct blood smoothly through the dividers.

10. The invention according to claim 2 comprising a shoulder on both sides of said socket-chamber profiled identical to the chamber opening but larger, providing a means for placing and sealing the membrane cartridges in close proximity to the full height of said slit penetrating the dividers.

11. The invention according to claim 2 further comprising a plurality of pressure relief valves in the top of the membrane cartridges, a pair of through-holes in upper end of said chamber, providing a means for pressure relief valves to seal in said socket chambers and divert waste products from inside the membrane cartridges up and outside said chamber.

12. The invention according to claim 2 further comprises vertical waste drains ports in upper end of said chambers, where radiuses come together over said dividers, forming an inward facing crease, which combined with said vertical port, forms drain ports for plasma waste products expelled from membrane pressure relief valves in membrane cartridges, thereby providing means to move waste products from the membrane cartridges to the urine collection area below membrane chamber profiles in said housing support frame.

13. The invention according to claim 2 comprising a plurality of dual membrane cartridges having dual semipermeable reverse osmosis membranes, said cartridge sized to fit and seal in said chambers, with one dual membrane cartridge placed and sealed on each side of said narrow blood distribution slit through each divider.

14. The invention according to claim 2 comprising a plurality of osmosis diffusion membranes placed and sealed in said housing for the selection of molecules from a stored filtrate, diffusing said molecules into a blood plasma, for returning to a patient's blood stream.

15. A human kidney replacement unit for patients with end stage renal disease, comprising:

a housing;

a main support frame mounted inside the housing and having a plurality of chambers;

an arterial inlet tube sealingly mounted to one side of the housing for transporting a bloodstream from a human artery into the housing;

a venous outlet tube sealingly mounted to another side of the housing for transporting the bloodstream out of the housing and into a human vein;

a waste discharge tube sealingly mounted to a lower side of the housing for transporting a waste-stream out of the housing and into a human ureter;

a plurality of semi-permeable, reverse-osmosis membrane cartridges; and a plurality of semi-permeable, osmosis diffusion membrane cartridges.

16. The human kidney replacement unit according to claim 15, wherein said plurality of semi-permeable, reverse-osmosis membrane cartridges comprising at least one matched pair are located in a chamber of the main support frame and housing.

17. The human kidney replacement unit according to claim 16, wherein said plurality of semi-permeable osmosis diffusion membrane cartridges comprising a least one matched pair are located in a chamber of the main support frame and housing that is adjacent to the chamber housing the matched pair of semi-permeable, reverse-osmosis membrane cartridges.

18. The human kidney replacement unit according to claim 15, wherein the support frame has slits and beveled channels, which are free of sharp corners and edges to reduce fluid turbulence.

* * * * *

UNITED STATES PATENT AND TRADEMARK OFFICE
CERTIFICATE OF CORRECTION

PATENT NO. : 7,083,653 B2  Page 1 of 1
APPLICATION NO. : 10/916586
DATED : August 1, 2006
INVENTOR(S) : Charles E. Jennings It is certified that error appears in the above-identified patent and that said Letters Patent is hereby corrected as shown below:

On the Title page item (76), should read: Charles Edward Jennings
12002 Gettysburg Court
Tomball, TX 77377

Signed and Sealed this

Thirty-first Day of March, 2009

JOHN DOLL
*Acting Director of the United States Patent and Trademark Office*